United States Patent
Bublewitz et al.

(12) 
(10) Patent No.: US 6,394,643 B1
(45) Date of Patent: May 28, 2002

(54) DEVICE FOR MIXING TWO PASTY MATERIALS, ESPECIALLY FOR MIXING A DENTAL IMPRESSION MATERIAL WITH A CATALYST MATERIAL

(75) Inventors: Alexander Bublewitz, Herborn; Matthias Suchan, Hachenburg, both of (DE)

(73) Assignee: Kettenbach GmbH & Co. KG, Eschenburg (DE)

(*) Notice: Subject to any disclaimer, the term of this patent is extended or adjusted under 35 U.S.C. 154(b) by 0 days.

(21) Appl. No.: 09/807,503

(22) PCT Filed: Oct. 14, 1999

(86) PCT No.: PCT/EP99/07703

§ 371 (c)(1),
(2), (4) Date: Apr. 16, 2001

(87) PCT Pub. No.: WO00/21652

PCT Pub. Date: Apr. 20, 2000

(30) Foreign Application Priority Data

Oct. 14, 1998 (DE) .......................................... 298 18 280

(51) Int. Cl.[7] ................................ B01F 5/04; B01F 7/00
(52) U.S. Cl. ................. 366/172.1; 366/312; 366/326.1; 366/329.1; 222/145.6
(58) Field of Search ........................... 366/172.1, 172.2, 366/176.1, 181.5, 312, 325.1, 325.2, 326.1, 329.1, 329.2; 222/145.5, 145.6

(56) References Cited

U.S. PATENT DOCUMENTS

| | | | |
|---|---|---|---|
| 3,051,455 A | * | 8/1962 | Magester |
| 3,226,093 A | * | 12/1965 | Gugel et al. |
| 3,302,832 A | * | 2/1967 | Hardman et al. |
| 3,390,814 A | * | 7/1968 | Creighton, Jr. et al. |
| 3,570,719 A | * | 3/1971 | Schiff |
| 3,587,982 A | * | 6/1971 | Campbell |
| 3,711,067 A | * | 1/1973 | Kovacs |
| 3,767,085 A | * | 10/1973 | Cannon et al. |

(List continued on next page.)

FOREIGN PATENT DOCUMENTS

| | | | |
|---|---|---|---|
| DE | 2949369 | * | 6/1981 |
| DE | 4235736 | * | 3/1994 |
| DE | 29705741 | * | 8/1998 |
| DE | 29705741 | * | 9/1998 |
| DE | 10015133 | * | 8/2001 |
| EP | 87029 | * | 8/1983 |
| EP | 492412 | * | 7/1992 |
| EP | 603492 | * | 6/1994 |
| EP | 1072323 | * | 1/2001 |
| EP | 1110599 | * | 6/2001 |
| EP | 1149627 | * | 10/2001 |
| JP | 6-226178 | * | 8/1994 |
| JP | 8-187727 | * | 7/1996 |
| JP | 2001-207996 | * | 8/2001 |
| WO | 95/22402 | * | 8/1995 |
| WO | 01/24919 | * | 4/2001 |

Primary Examiner—Charles E. Cooley
(74) Attorney, Agent, or Firm—Diller, Ramik & Wight

(57) ABSTRACT

A device for mixing two pasty substances is provided with a housing including an essentially tubular section having two radial inlet openings at a rear end and an outlet opening at a front end of the tubular section, and a driveable mixer shaft extending through the tubular section and rotatably supported in the housing. The mixer shaft includes multiple rigid mixer elements protruding from an axis for mixing the two pasty substances when they pass through the tubular section. The mixer shaft includes at the level of the inlet openings at least one deflection element for promoting the axial transportation of the two pasty substances when fed through the inlet openings, wherein the at least one deflection element has a deflection surface extending about the axis and at an inclination to a radial plane of the axis.

22 Claims, 3 Drawing Sheets

U.S. PATENT DOCUMENTS

| | | | | |
|---|---|---|---|---|
| 4,107,793 | A | * | 8/1978 | Wallace |
| 4,432,469 | A | * | 2/1984 | Eble et al. |
| 4,471,888 | A | * | 9/1984 | Herb et al. |
| 4,767,025 | A | * | 8/1988 | Gebauer et al. |
| 4,934,827 | A | * | 6/1990 | Taschke et al. |
| 4,951,843 | A | * | 8/1990 | Paetow |
| 5,249,862 | A | * | 10/1993 | Herold et al. |
| 6,244,740 | B1 | * | 6/2001 | Wagner et al. |
| 6,311,871 | B1 | * | 11/2001 | Binder |

* cited by examiner

DEVICE FOR MIXING TWO PASTY MATERIALS, ESPECIALLY FOR MIXING A DENTAL IMPRESSION MATERIAL WITH A CATALYST MATERIAL

BACKGROUND OF THE INVENTION

The invention relates to a device for mixing two pasty substances which are in particular a dental impression substance and a catalyst substance for accelerating polymerization of the dental impression substance.

The device according to the invention is attached onto the two outlet stubs of a discharge device, via which the pasty substances are fed to the mixing device by application of pressure, and after mixing in the mixing device the pasty substances are discharged in the form of a mixture.

In several technical applications it is necessary to apply two separately stored pasty substances in form of a mixture. For this purpose either dynamical or statical continuous mixers are used which mix the substances with each other when the pasty substances flow through a mixer housing. A dynamical mixer is known from EP-A-0 492 412. This known device comprises an essentially tubular mixer housing with a mixer shaft rotatably arranged therein. The mixer shaft comprises a plurality of radially protruding web-shaped mixer elements which, when the mixer shaft is driven, serve for deflection of the substance flows thus mixing the two pasty substances with each other. The pasty substances are fed via a radial front wall at the rear end of the mixer housing into the latter. For this purpose the front wall comprises two inlet stubs which are attached onto the outlet stubs of a device for discharging the pasty substances.

To prevent contamination in the direction of the outlet stubs of the discharge device the known mixer comprises stripping elements protruding from the mixer shaft, the stripping elements moving along the inner side of the rear-side front wall and transporting pasty material entering via the inlet stubs to the side. The pasty material supplied via one of the inlet stubs inside the housing is at least partially transported in circumferential direction by said strippers thus being fed to the area of the other inlet stub where contamination in the direction of the inlet stub and further in the direction of the outlet stub of the respective discharge device connected with the inlet stub may occur when the dynamic mixer is not driven.

SUMMARY OF THE INVENTION

It is an object of the invention to provide a device for mixing two pasty substances where the risk of contamination in backward direction is reduced.

To solve this object the invention suggests a device for mixing two pasty substances, the device comprising

- a housing comprising an essentially tubular section having two radial inlet openings for the two pasty substances at the rear end and an outlet opening for the mixed pasty substances at the front end of the tubular section,
- a driveable mixer shaft extending through the tubular section and rotatably supported in the housing,
- wherein the mixer shaft comprises a plurality of rigid mixer elements protruding from an axis, the mixer elements serving for mixing the two pasty substances during their passage through the tubular section of the housing.

According to the invention said device is characterized in that the mixer shaft comprises at the level of the inlet openings at least one deflection element for promoting the transport in axial direction of the pasty substances fed through the inlet openings to the tubular section of the housing, wherein the at least one deflection element comprises a deflection surface extending about the axis and at an inclination to a radial plane of the axis.

In the mixing device according to the invention (hereinafter referred to as dynamic mixer) the pasty substances to be mixed are radially supplied to the essentially tubular section of the mixer housing. For this purpose the tubular section of the housing is provided with two radial inlet openings in particular arranged diametrically opposite each other. The pasty substance flows fed to the mixer by application of pressure are supplied within the tubular section of the housing to at least one deflection element which extends about the axis of the mixer shaft. Said deflection element rotates together with the rotating mixer shaft and comprises a deflection surface extending at an inclination to a radial plane of the axis. In other words, the at least one deflection element is an essentially saw-tooth wedge extending in an arcuate manner about the axis of the mixer shaft. Said deflection element acts in the same way as a screw conveyor in a screw-type pump and ensures that the incoming pasty material is directly transported in axial direction from the inlet openings towards the outlet opening. This reliably prevents contamination in backward direction since the at least one deflection element always promotes the axial transport of the pasty substances fed through the inlet openings to the tubular section of the mixer housing.

As already said above, the deflection element can be of wedge-type configuration. Alternatively to this wedge form the deflection element can be designed as a web extending helically about the axis; in this embodiment the deflection element is configured as a thread. Such helical webs are known from screw-type pumps and screw conveyors.

Advantageously, at the level of the radial inlet openings of the tubular section of the housing two deflection elements are provided on the axis, the deflection elements appropriately being arranged diametrically opposite each other. Said deflection elements or each deflection element preferably extends over an angular range of 180° to 90°.

To be able to attach the dynamic mixer according to the invention onto the two outlet stubs of a squeezing device, the housing comprises at its rear end an insertion part oriented at an inclination to the axis, on which insertion part two inlet stubs are protrudingly arranged. Said insertion part is located in a flared housing section of the mixer joining the tubular section, and comprises two ducts extending from the inlet stub. Said two ducts radially extend, at an angle, to a central cylindrical deepened reception portion on the inner side of the insertion part, which deepened portion receives the axis of the mixer shaft with the at least one deflection element. Thus the cylindrical deepened reception portion of the insertion part forms a portion of the tubular housing section of the mixer.

According to a preferred aspect of the invention a plurality of mixer elements are located between the radial inlet openings and the axial outlet opening within the tubular housing section, said mixer elements protruding in the form of radial webs from the axis and extending up to near the inner surfaces of the tubular housing section. Within several radial planes said mixer elements are arranged such that they protrude from the shaft, which results in deflection of substance flows axially extending through the housing. This leads to the desired mixing effect. The mixing effect is intensified when said mixer elements, which prevent direct flow between the inlet openings and the outlet opening due to their radial orientation, extend over a larger angular range, e.g. 90°. This can be realized by connecting adjacent mixer elements via a circumferential portion. In this way, mixer elements in the form of quarter circles are configured, wherein it may be of advantage if the middle sections of these quarter circles, as seen in circumferential direction, protrude from the inner surface of the tubular section of the housing to a larger extent than their ends. It is appropriate if two adjacent radially extending mixer elements staggered from radial plane to radial plane, as seen in circumferential direction, are connected with each other in the manner described above.

Besides arrangement of the rigid mixer elements as described above it is of advantage with regard to the mixing process if the mixer shaft comprises additional flexible stripper elements which move along the inner wall of the tubular housing due to their flexible configuration or at least due their flexible free ends arranged at a distance to the axis. Hereunder an embodiment of the invention is explained in detail with reference to the drawings in which:

DESCRIPTION OF THE PREFERRED EMBODIMENTS

Figure 1:
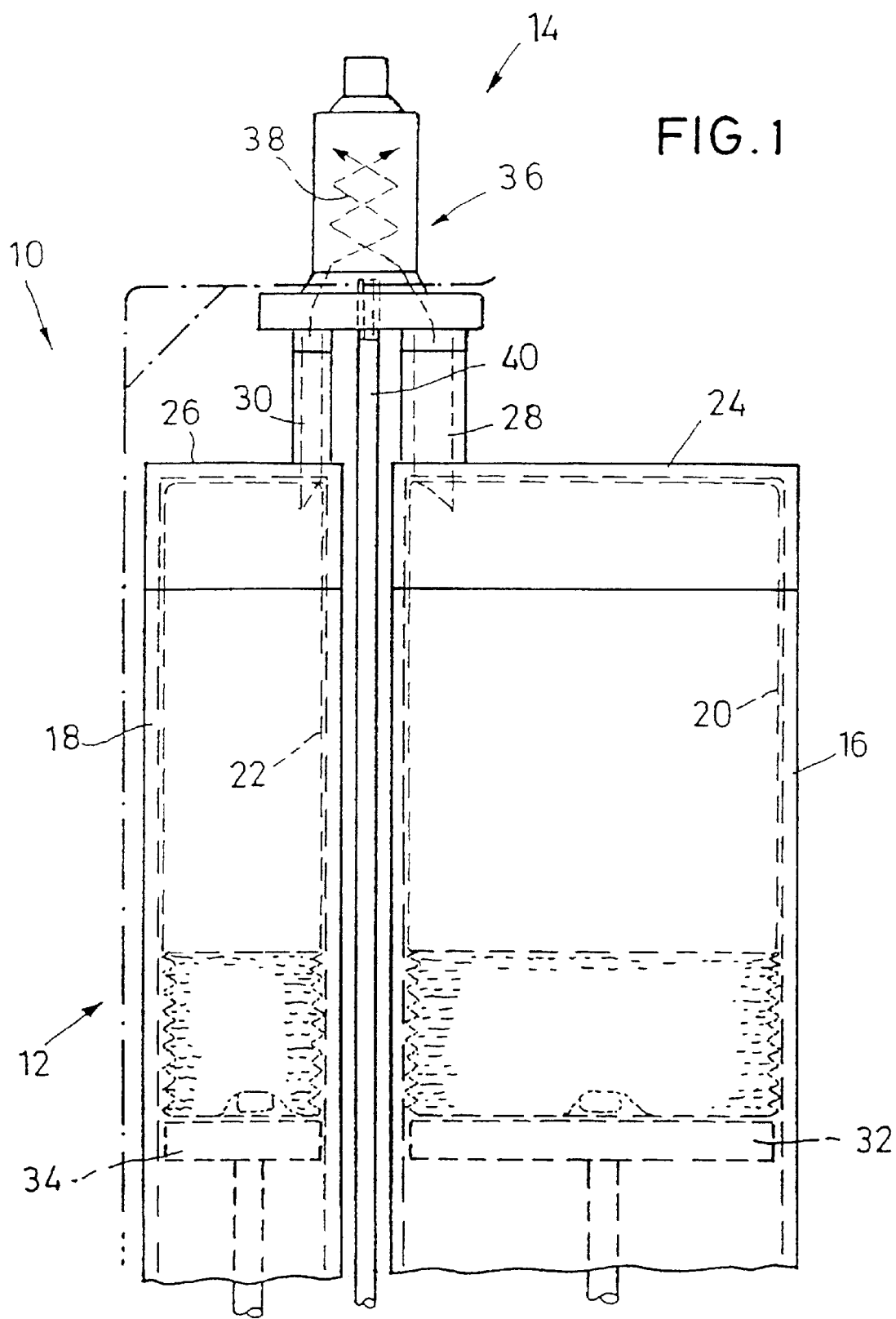
FIG. 1 shows a general side view of a discharge device for mixed pasty components.

FIG. 1 shows a side view of a discharge device 10 for two pasty components to be mixed with each other. Said device 10 comprises a squeezing part 12 and a mixing part 14, said squeezing part 12 having two pressure containers 16, 18 for receiving two bags 20,22 containing the pasty substances. At the front ends 24,26 of the pressure containers 16,18 the latter comprise outlet stubs 28,30 via which the contents of the bags 20,22 is discharged when pressure is applied to the rear end of the bags 20,22. Pressure is applied to the bags 20,22 by means of motor-driven pressure stamps 32,34, which is not shown in detail here.

Onto the outlet stubs 28,30 a dynamic mixer 36 is attached which is hereunder described in detail with reference to FIGS. 2 to 7. Concerning said dynamic mixer 36 it can generally be said that its mixer shaft 38 is driven by a motor. For this purpose the mixer shaft 38 is adapted to be coupled with a drive rod 40 which is rotatingly driven by a motor which is not shown either.

Figure 2:
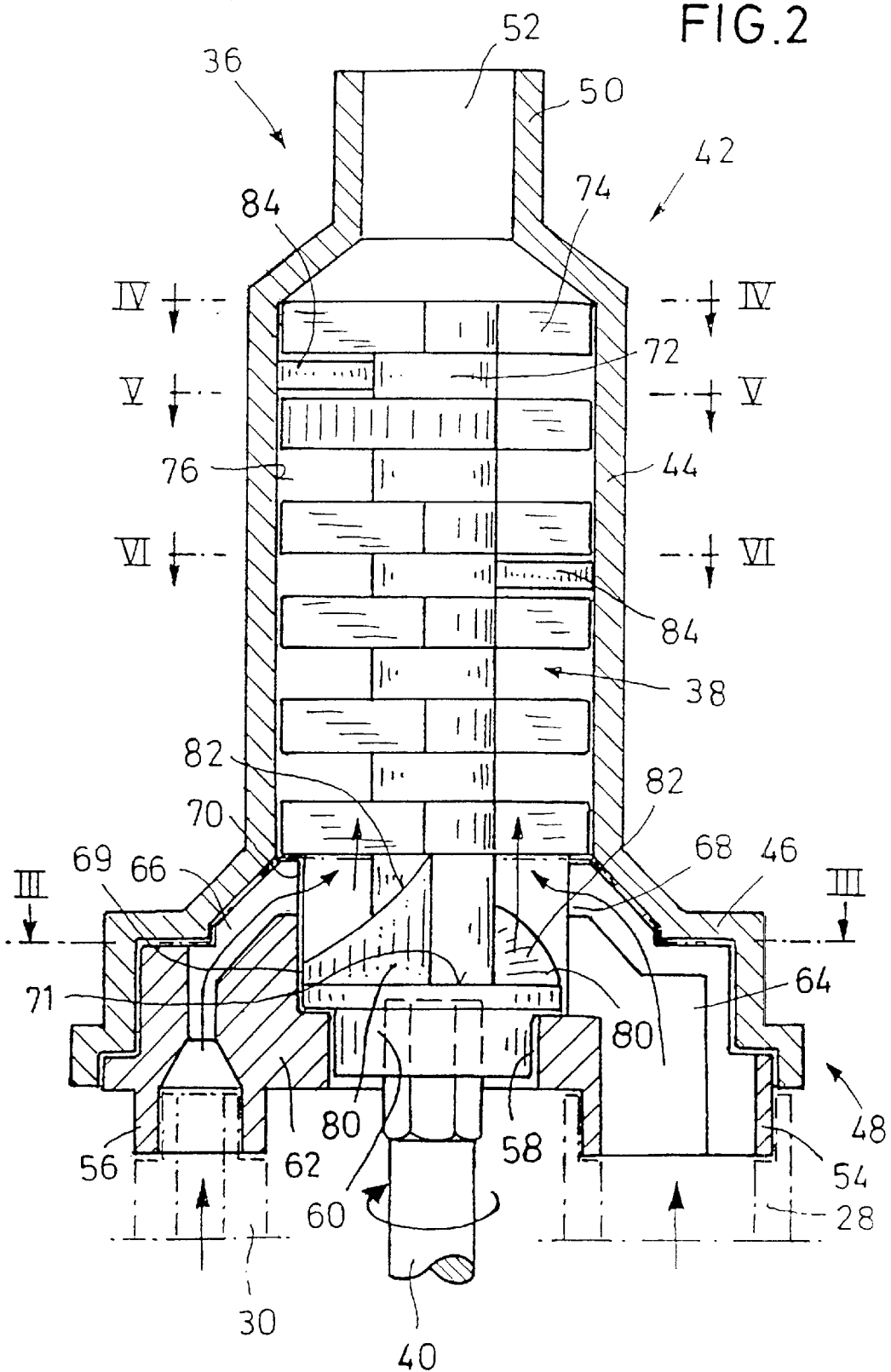
FIG. 2 shows a longitudinal section of the dynamic mixer used for the discharge device shown in FIG. 1, FIGS. 3 to 6 show cross-sections of the mixer shown in FIG. 2 along the lines III—III, IV—IV, V—V and VI—VI.

The details of the dynamic mixer 36 are shown in FIG. 2. This figure shows a longitudinal section of the mixer 36. The mixer 36 comprises a housing 42 which has an essentially cylindrical or tubular section 44 with a flared end section 46 at the rear end 48 facing the squeezing part 12, and a tapered front end 50. Said tapered end 50 is designed as outlet stub and defines the outlet opening 52 for the material mixture, while at the rear end 48 of the housing 42 two inlet stubs 54,56 are arranged which are adapted to be attached onto the outlet stubs 28,30 of the squeezing part 12. Between the two inlet stubs 54,56 a passage 58 is provided in which one end 60 of the mixer shaft 38 is rotatably supported. Via said passage the drive rod 40 can be coupled with the mixer shaft 38.

The inlet stubs 54,56 and the passage 58 are configured in an insertion part 62 which is inserted into the flared section 46 at the rear end 48 of the housing 42. Proceeding from the inlet stubs 54,56 two ducts 64,66 extend through the insertion part 62, the ducts being deflected and ending in radial openings 68,70. Said inlet openings 68,70 are radially arranged relatively to the cylindrical section 44 of the mixer housing 42. Via the ducts 64,66 the two pasty components are transported into the dynamic mixer 36 where they are fed in radial direction to the mixer shaft 38.

Figure 3:
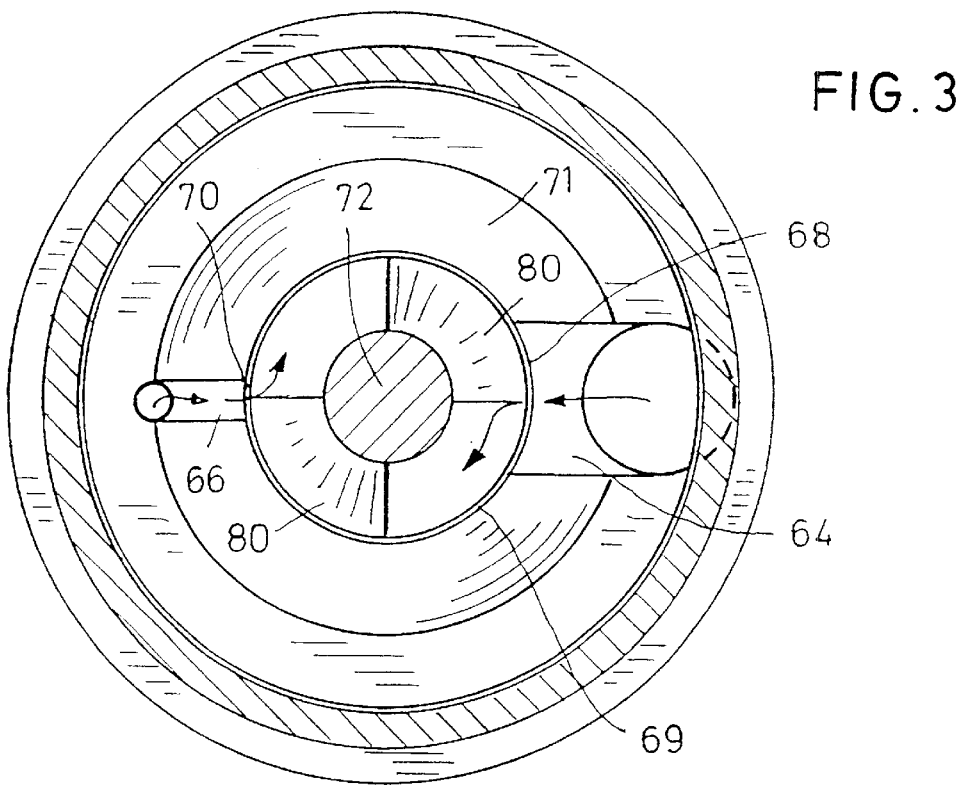
Figure 4:
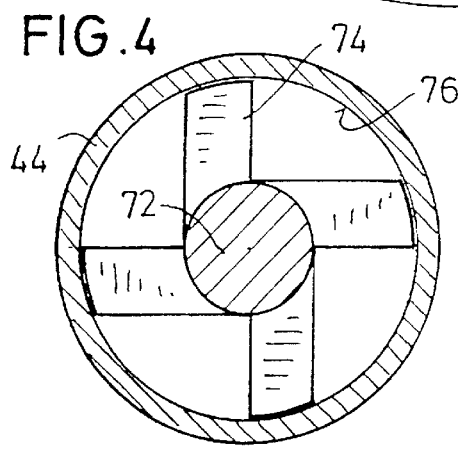
Figure 5:
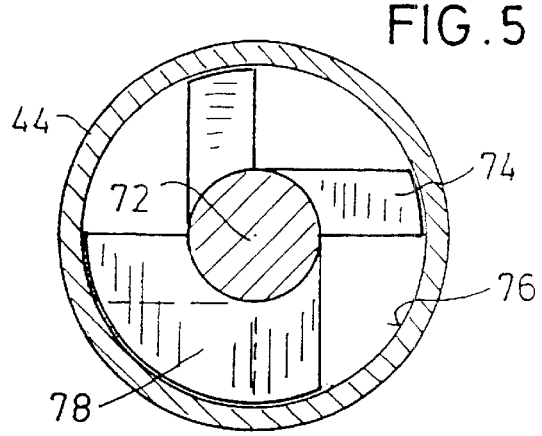

As can be seen in FIGS. 2 and 3 the insertion part 62 comprises a central essentially cylindrical deepened reception portion 69 which is arranged concentrically to the passage 58 and into which the mixer shaft 38 is inserted. In the cylindrical wall 71 of the deepened reception portion 69 the inlet openings 68,70 are provided. Further, the ducts 64,66 are configured in this area. Said ducts 64,66 are configured as grooves or recesses which are open at the top and which, together with the essentially flared housing section 46, form the ducts closed on all sides.

The mixer shaft 38 comprises a rotatably supported axis 72 from which, in a plurality of radial planes, four web-type mixer elements 74 each protrude essentially in radial direction. The exact arrangement of said mixer elements 74 is shown in the sectional representation of FIG. 4. It can be seen that the mixer element 74 limiting side edges lying in the circumferential direction extend essentially tangentially to the circumferential surface of the axis 72. According to FIG. 4 four mixer elements 74 are provided for each radial plane, the mixer elements 74 reaching up to near the inner surface 76 of the cylindrical housing section 44 as is shown in FIG. 2. The overall area between the inlet openings 68,70 and the end of the mixer shaft 38, which extends up to the tapered end 50 of the mixer housing 42, is provided with said mixer elements 74. Further, the mixer shaft 38 comprises mixer elements 78 configured as quarter circuit areas which are formed by connecting two adjacent mixer elements 74 of a radial plane (see, for example, the sectional representation of FIG. 5). In this embodiment the radially outer limiting edge of the mixer element 78 is of circular arc configuration, while it extends secantially in the alternative shown in FIG. 7. The mixer element 78' shown in FIG. 7 thus comprises, in a middle circumferential section, a larger section towards the inner surface 76 of the cylindrical housing section 44.

While the mixer elements 74,78,78', owing to their radial extension up to near the cylindrical housing section 44, ensure deflection and thus swirling of the axially flowing pasty substances when the mixer shaft 38 rotates, the mixer shaft 38 comprises in the area of the radial inlet openings 68,70 two deflection elements 80 configured in the form of a screw conveyor. The deflection elements 80 are designed as saw-tooth wedges extending over approximately 90° about the axis 72 of the mixer shaft 38. Said deflection elements 80 have a deflection surface 82 ascending in circumferential direction, said deflection surface 82 being directed towards the outlet end 52 of the dynamic mixer 36 and extending at an angle to a plane extending radially to the axis 72. Said deflection elements 80 thus extend helically in sections and provide an axial movement component of the pasty substance flows. Thus the deflection elements 80 promote the removal of a pasty substance entering the cylindrical housing section 44 via the inlet openings 68,70. This promoted and thus intensified removal of the pasty substances in axial direction reduces the danger of contamination of the two pasty substances, i.e. the undesired mixing of the two pasty substances or their contamination in the direction of the inlet openings 68,70 into the ducts 64,66 and possibly up to the outlet stubs 28,30. If contamination and thus polymerization occurs in these areas, it is no longer possible to discharge any residual material of the bags 20,22 owing to clogged outlet stubs 28,30.

Figure 6:
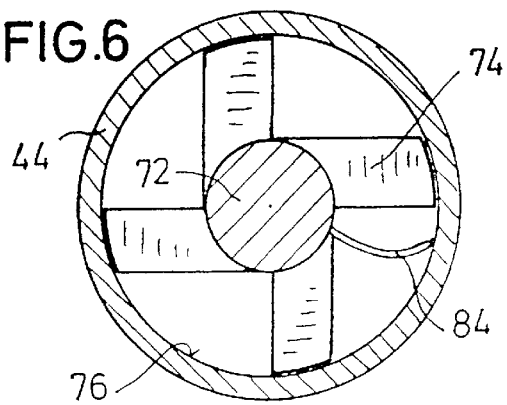
Figure 7:
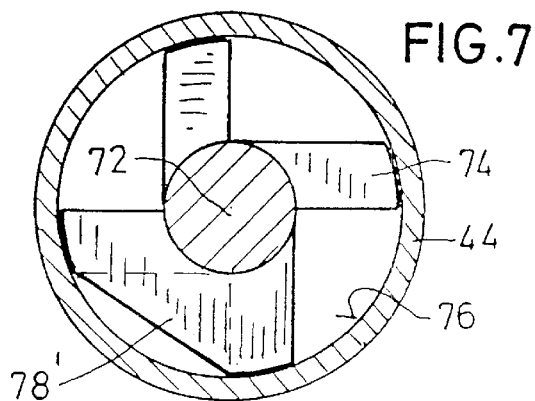
FIG. 7 shows a cross-section similar to that of FIG. 6 but of an alternative embodiment of the mixer shaft.

Another feature of the dynamic mixer 36 is to be explained with reference to FIG. 6. The mixer elements 74 described above are of rigid configuration and essentially radially protruding webs which cause swirling of the substance flows due to rotation of the axis 72. In addition to the rigid mixer elements 74 the dynamic mixer 36 comprises further mixer elements 84 designed as thin and flexible webs, said mixer elements 84 moving from the inside along the inner side 76 of the cylindrical housing section 44. These additional flexible mixer elements 84, too, cause swirling of the substance flows. One flexible mixer element 84 per plane is provided in a plurality of contiguous radial planes of the mixer shaft 38, said mixer elements 84 being staggered from radial plane to radial plane by a constant angular range. The same applies to the mixer elements 78 and 78', respectively, which connect two adjacent mixer elements 74 and are also staggered from radial plane to radial plane, in this case by 90°. Said mixer elements 84 and the mixer elements 78 and 78', respectively, are thus uniformly distributed along a helical line about the axis 72. Both types of mixer elements are very well suited for homogeneous mixing of pasty substances in a dynamic mixer 36 which can also be referred to as continuous mixer.

Although a preferred embodiment of the invention has been specifically illustrated and described herein, it is to be understood that minor variations may be made in the apparatus without departing from the spirit and scope of the invention, as defined the appended claims.

What is claimed is:

1. A device for mixing two pasty substances comprising housing (42) including a substantially tubular section (44), said substantially tubular section (44) having two inlet openings (68, 70), each for receiving a pasty substance at a rear end (48) of the housing (42) and an outlet opening (52) for discharging an admixed pasty substance from a front end of the tubular section (44), a rotatable mixer shaft (38) extending into the tubular section (44) and being rotatably supported in the housing (42), the mixer shaft (38) including a plurality of rigid mixer elements (74) protruding from an axis (72) thereof for admixing the two pasty substances during their passage through the tubular section (44), an annular insertion part (62) within the rear end (48) of the housing (42) disposed substantially concentric to the axis (72), the insertion part (62) including an inner surface facing the tubular section (44) of the housing (42) and an outer surface forming the rear end (48) of the housing (42), said rear end (48) of the housing (42) having two inlet stubs (54, 56), said mixer shaft (38) including a mixer shaft portion adjacent the inlet openings (68, 70) carrying at least one deflection element (80) for deflecting the pasty substances fed through the inlet openings (68, 70) substantially axially into the tubular section (44) of the housing (42), said at least one deflection element (80) including a deflection surface (82) extending about the axis (72) and at an inclination to a radial plane thereof, the insertion part (62) being provided with a cylindrical recess (69) housing said mixer shaft portion and the at least one deflection element (80), two ducts (64, 66) extending from said two inlet stubs (54, 56) to said inlet openings (68, 70), and said two ducts (64, 66) open substantially radially into said cylindrical recess (69).

2. The mixing device as defined in claim 1 wherein the at least one deflection element (80) is of a wedge configuration.

3. The mixing device as defined in claim 2 wherein the at least one deflection element (80) is defined by two deflection elements (80, 80) disposed in diametrically opposite relationship to each other and to the axis (72).

4. The mixing device as defined in claim 2 wherein the at least one deflection element (80) is defined by two deflection elements (80, 80) extending over an angular range of between 90° to 180°.

5. The mixing device as defined in claim 4 wherein said tubular section (44) includes an inner surface (76), and an identical number of said mixer elements (74) lie as a group within each of a plurality of radial planes of the axis (72) and extend contiguous to the inner surface (76) of the tubular section (74).

6. The mixing device as defined in claim 2 wherein the at least one deflection element (80) includes a deflection surface (82) extending helically about the axis (72).

7. The mixing device as defined in claim 6 wherein said tubular section (44) includes an inner surface (76), and an identical number of said mixer elements (74) lie as a group within each of a plurality of radial planes of the axis (72) and extend contiguous to the inner surface (76) of the tubular section (74).

8. The mixing device as defined in claim 2 wherein said tubular section (44) includes an inner surface (76), and an identical number of said mixer elements (74) lie as a group within each of a plurality of radial planes of the axis (72) and extend contiguous to the inner surface (76) of the tubular section (74).

9. The mixing device as defined in claim 1 wherein the at least one deflection element (80) is defined by two deflection elements (80, 80) disposed in diametrically opposite relationship to each other and to the axis (72).

10. The mixing device as defined in claim 9 wherein the at least one deflection element (80) is defined by two deflection elements (80, 80) extending over an angular range of between 90° to 180°.

11. The mixing device as defined in claim 10 wherein said tubular section (44) includes an inner surface (76), and an identical number of said mixer elements (74) lie as a group within each of a plurality of radial planes of the axis (72) and extend contiguous to the inner surface (76) of the tubular section (74).

12. The mixing device as defined in claim 9 wherein the at least one deflection element (80) includes a deflection surface (82) extending helically about the axis (72).

13. The mixing device as defined in claim 12 wherein said tubular section (44) includes an inner surface (76), and an identical number of said mixer elements (74) lie as a group within each of a plurality of radial planes of the axis (72) and extend contiguous to the inner surface (76) of the tubular section (74).

14. The mixing device as defined in claim 9 wherein said tubular section (44) includes an inner surface (76), and an identical number of said mixer elements (74) lie as a group within each of a plurality of radial planes of the axis (72) and extend contiguous to the inner surface (76) of the tubular section (74).

15. The mixing device as defined in claim 1 wherein the at least one deflection element (80) is defined by two deflection elements (80, 80) extending over an angular range of between 90° to 180°.

16. The mixing device as defined in claim 15 wherein the at least one deflection element (80) includes a deflection surface (82) extending helically about the axis (72).

17. The mixing device as defined in claim 16 wherein said tubular section (44) includes an inner surface (76), and an identical number of said mixer elements (74) lie as a group within each of a plurality of radial planes of the axis (72) and extend contiguous to the inner surface (76) of the tubular section (74).

18. The mixing device as defined in claim 15 wherein said tubular section (44) includes an inner surface (76), and an identical number of said mixer elements (74) lie as a group within each of a plurality of radial planes of the axis (72) and extend contiguous to the inner surface (76) of the tubular section (74).

19. The mixing device as defined in claim 1 wherein the at least one deflection element (80) includes a deflection surface (82) extending helically about the axis (72).

20. The mixing device as defined in claim 19 wherein said tubular section (44) includes an inner surface (76), and an identical number of said mixer elements (74) lie as a group within each of a plurality of radial planes of the axis (72) and extend contiguous to the inner surface (76) of the tubular section (74).

21. The mixing device as defined in claim 1 wherein said tubular section (44) includes an inner surface (76), and an identical number of said mixer elements (74) lie as a group within each of a plurality of radial planes of the axis (72) and extend contiguous to the inner surface (76) of the tubular section (74).

22. The mixing device as defined in claim 21 wherein at least two mixer elements (74, 74) in the same radial plane are connected to each other by a circumferential portion (78, 78').

* * * * *